United States Patent [19]

Runge

[11] Patent Number: 5,300,015

[45] Date of Patent: Apr. 5, 1994

[54] BLOOD CONDUIT FOR PULSATILE CARDIOPULMONARY BYPASS PUMP

[76] Inventor: Thomas M. Runge, 2630 Exposition Blvd., Austin, Tex. 78703

[21] Appl. No.: 845,017

[22] Filed: Mar. 3, 1992

[51] Int. Cl.⁵ ............................................. A61M 1/03
[52] U.S. Cl. ........................................ 600/16; 623/3
[58] Field of Search ............. 600/16, 17; 128/DIG. 3, 128/DIG. 12; 623/3

[56] References Cited

U.S. PATENT DOCUMENTS

| | | | |
|---|---|---|---|
| 3,198,385 | 8/1965 | Maxwell | 128/DIG. 12 X |
| 3,949,734 | 4/1976 | Edwards et al. | 128/DIG. 3 X |
| 4,080,958 | 3/1978 | Bregman et al. | 600/16 |
| 4,143,425 | 3/1979 | Runge | 623/3 |
| 4,250,872 | 2/1981 | Tamari | 600/16 |
| 4,293,961 | 3/1980 | Runge | 623/3 |
| 5,147,281 | 9/1992 | Thornton et al. | 600/16 |

*Primary Examiner*—Lee S. Cohen
*Assistant Examiner*—Jeffrey R. Jastrzab
*Attorney, Agent, or Firm*—Brady, O'Boyle & Gates

[57] ABSTRACT

A blood conduit for a pulsatile cardiopulmonary bypass pump constructed and arranged to provide a surge chamber, a pumping chamber, and a reservoir portion. The blood conduit precludes the necessity of employing a separate reservoir in a closed cardiopulmonary bypass system so that there is a direct continuity of blood from the atrium of the patient's heart to the pulsatile pump. With a preload responsive pulsatile pump, the system can be utilized with a gravity flow oxygenator.

2 Claims, 4 Drawing Sheets

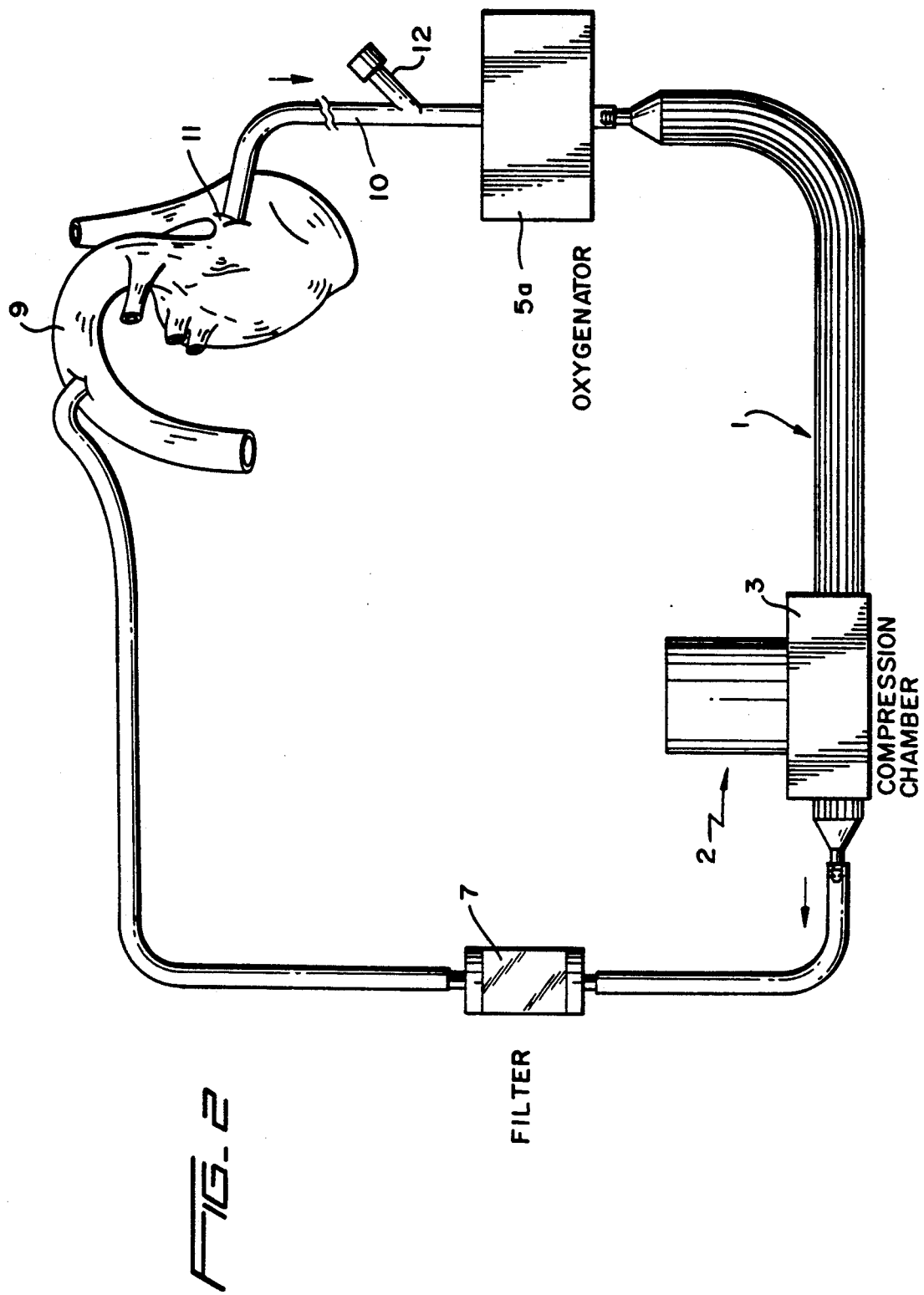

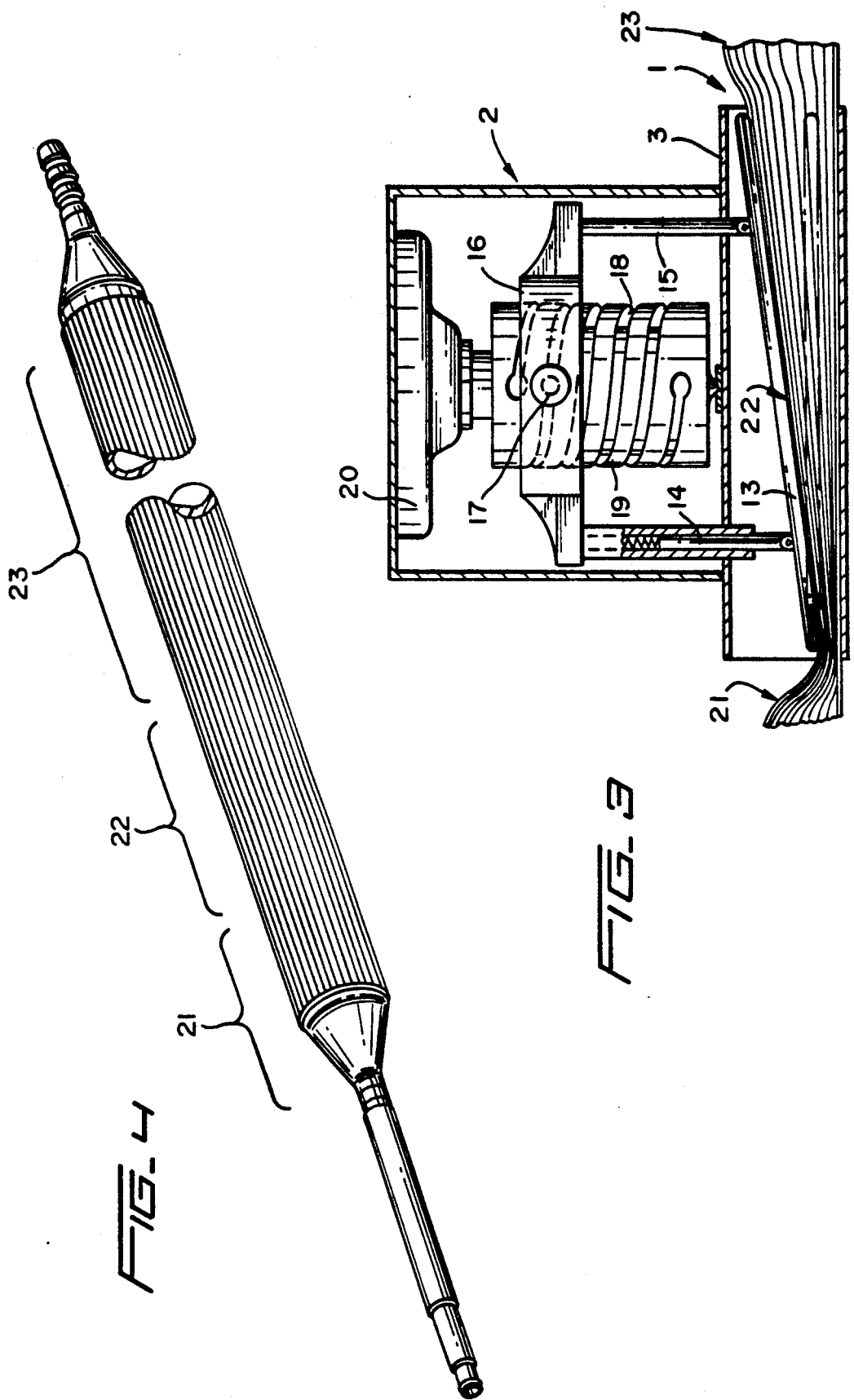

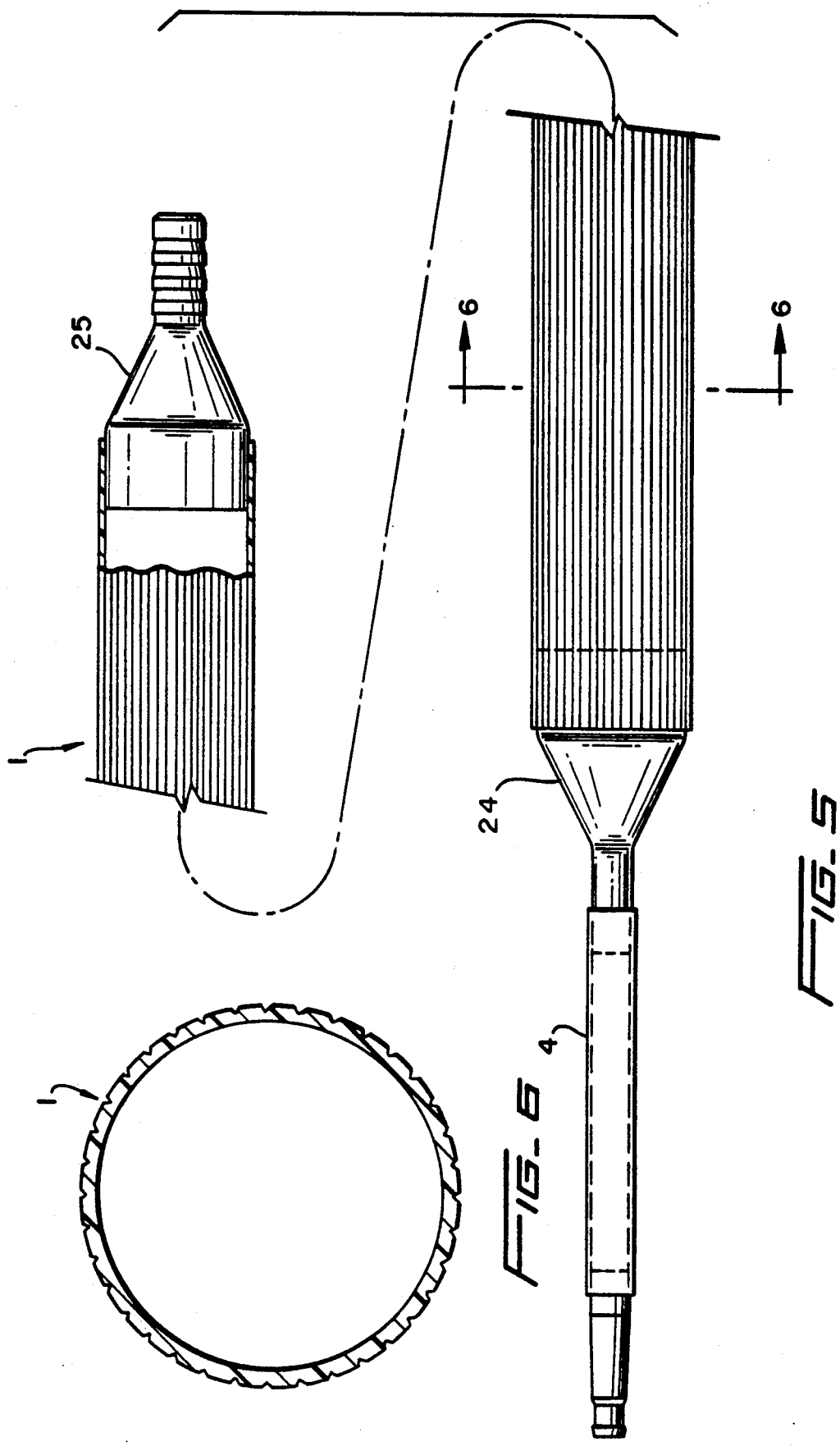

BLOOD CONDUIT FOR PULSATILE CARDIOPULMONARY BYPASS PUMP

BACKGROUND OF THE INVENTION

In conventional cardiopulmonary bypass systems, blood is taken from the patient's heart and passed through an oxygenator whereby the blood is oxygenated as a substitute for the functions normally performed by the patient's lungs which have been bypassed during the surgery. A blood pump, filters and reservoirs are also included in the system, whereby the oxygenated blood is circulated through the heart. The reservoirs are usually placed in the blood flow circuit between the right atrium and the inlet to the blood pump. While these systems have been commonly employed for years, the use of reservoirs has resulted in certain disadvantages. The use of reservoirs adds another component to the system, thereby increasing the cost of the system as well as trauma to the blood by contacting air and foreign material. Also, increased priming volume is needed when reservoirs are employed, usually a crystalloid solution, resulting in dilution and diminished oxygen carrying capacity of the patient's blood.

SUMMARY OF THE INVENTION

To preclude the necessity of employing a reservoir in cardiopulmonary bypass system, the blood conduit of the present invention has been devised to replace the conventional in-line reservoir, whereby there is a direct connection from the atrium to a preload responsive pulsatile pump, uninterrupted by a reservoir, resulting in more precise response of the pump to atrial volume. There is less trauma to blood because of the reduction of contact area with foreign material and reservoir air, and by omitting the reservoir priming volume is reduced, making the potential for mandatory blood replacement less.

The conduit of the present invention comprises a tube of biocompatible polymer such as Polyvinyl chloride, or PELLETHANE@ manufactured by Dow, Inc. The tube is constructed and arranged to provide a pumping chamber, a reservoir portion, and a vertical portion for enhancing flow velocity and volume into the reservoir portion.

BRIEF DESCRIPTION OF THE DRAWINGS

FIG. 2 is a view similar to FIG. 1 but showing the oxygenator positioned on the inlet side of the pump;

FIG. 3 is a sectional side elevational view of a pulsatile pump employed in the systems of FIGS. 1 and 2;

FIG. 4 is a perspective view of the conduit of the present invention;

FIG. 5 is a fragmentary, sectional side elevational view of the conduit shown in FIG. 4; and FIG. 6 is a view taken along line 6—6 of FIG. 5.

DESCRIPTION OF THE PREFERRED EMBODIMENT

Figure 1:
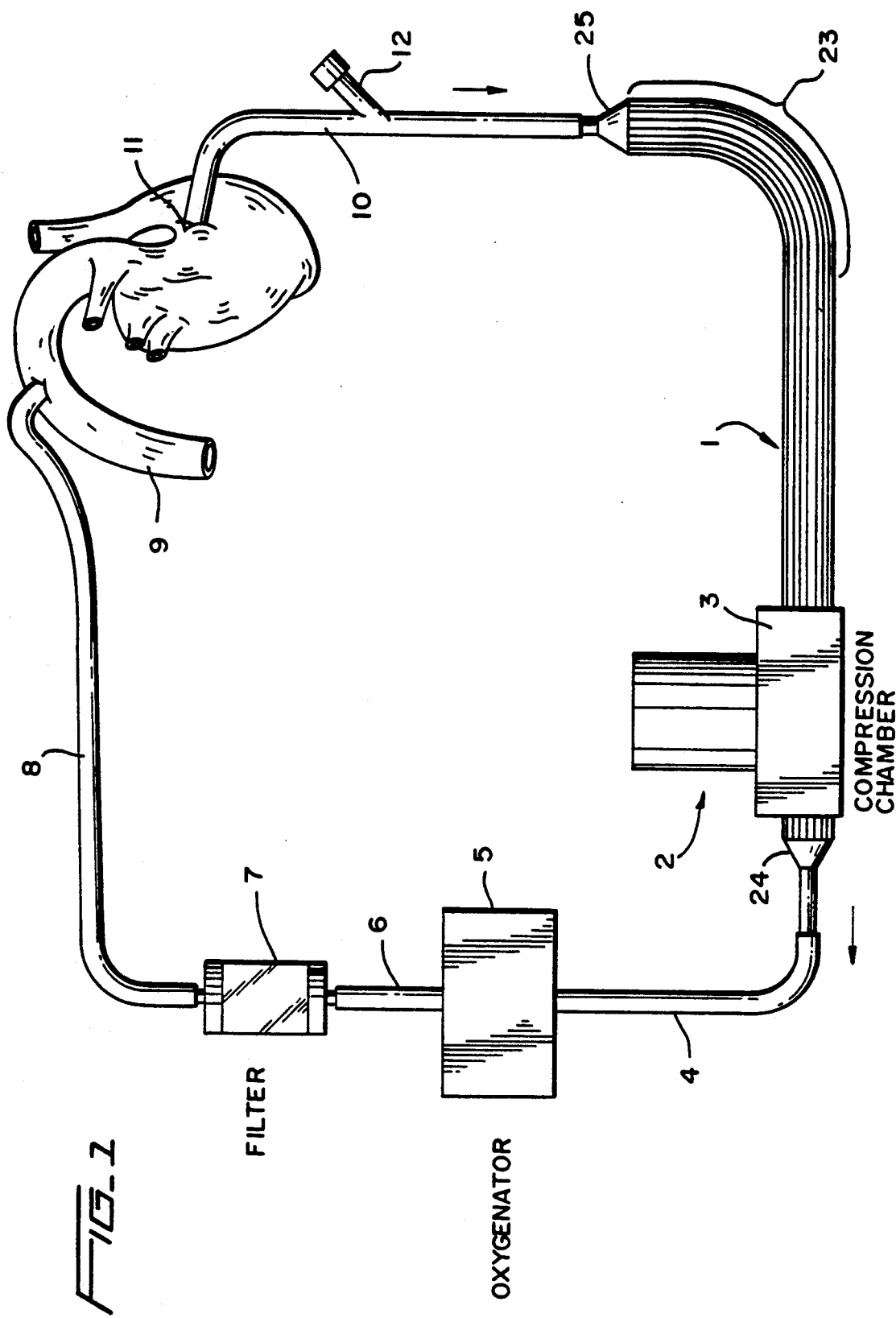
FIG. 1 is a diagrammatic view of a cardiopulmonary bypass system incorporating the conduit of the present invention and showing an oxygenator positioned on the outlet side of a pulsatile pump.

Referring to the drawings, and more particularly to FIG. 1, the conduit 1 of the present invention is adapted for use in a cardiopulmonary bypass system comprising a pulsatile pump 2 having a compression chamber 3 through which the conduit 1 extends. The pulsatile pump 2 pumps blood from the conduit 1 through a tube 4 connected to an oxygenator 5. The oxygenated blood flows from the oxygenator 5 through a line 6 to a filter 7. The oxygenated, filtered blood then flows through line 8 to the aorta 9 of the patient's heart. The blood then flows through a vertical tube 10 having one end connected to the heart atrium 11 and the other end connected to the inlet to the conduit 1. The tube 10 includes a port 12 for sampling the blood and adding arterial filter blood, thoracic suction blood, crystalloid and banked human blood or adding medication fluids to the flow circuit, or to function as a bubble trap for removing in-line air from an atrial tear or other source.

The system shown in FIG. 2 is similar to that of FIG. 1; however, the oxygenator 5a is placed in the blood flow circuit at the inlet end of the conduit 1 rather than at the outlet end as shown in FIG. 1, whereby a gravity flow membrane or other oxygenator can be employed.

The pulsatile pump 2, shown in FIG. 3, is of the general type disclosed in applicant's U.S. Pat. No. 4,143,425 or its modified configurations and includes a compression plate 13 positioned within the compression chamber 3 and engaging the exterior wall surface of the conduit 1, the pump's ventricle. A pair of legs 14 and 15 connect the compression plate 13 to a ring 16 having a follower pin 17 engaged within a helical groove 18 formed in a shaft 19 driven by a motor 20. Rotation of the shaft 19 will result in axial movement of the ring 16 thereon causing the plate 13 to compress the conduit in a manner disclosed in U.S. Pat. No. 4,143,425.

While the pulsatile pump 2 has been described as the type disclosed in U.S. Pat. No. 4,143,425, it could also be of the type disclosed in U.S. Pat. No. 4,553,532. In using the first type, the conduit 1 would include internal inlet and outlet valves of the type disclosed in said patent, and when using the second-mentioned pump, the inlet and outlet valves would be external of the conduit and be pinch type as disclosed in U.S. Pat. No. 4,553,532.

The details of the construction of the blood conduit 1 are illustrated in FIGS. 4, 5 and 6, wherein the blood conduit may include a surge chamber portion 21, a pumping chamber portion 22 and a reservoir portion 23, the pumping chamber portion 22 being positioned under the compression plate 13 of the pump 2 to form the ventricular portion of the conduit, as shown in FIG. 3, while the surge portion or chamber 21, which enhances the closure of the exit valve of the ventricular portion of the conduit, is positioned to the left of the pump and the reservoir portion 23 is positioned to the right of the pump. The main portion of the conduit which includes a portion of the surge chamber 21, the pumping chamber 22 and the reservoir portion 23 has a diameter of approximately 3.5 cm, a length of approximately 75 cm, and a thickness of 25 mils. Each end of the conduit is provided with an adapter or reducer 24 and 25 for connecting the conduit to the tubing 4 and 10, as shown in FIGS. 1 and 2, which have a diameter of approximately 1.26 cm. While adapters 24 and 25 are illustrated as separate components, the conduit 1 and adapters 24 and 25 can be molded in a single integral unit.

When connected into the system as shown in FIG. 1, the portion 23 of the conduit provides a blood reservoir for the pump 2, and the tube 10 provides a vertical portion for enhancing the blood flow velocity and volume into the reservoir portion 23.

From the above description, it will be appreciated by those skilled in the art that the construction and arrangement of the blood conduit of the present invention precludes the necessity of employing additional reservoirs in the system, whereby there is a direct connection from the atrium to the preload responsive pulsatile pump, thereby allowing the pump to be more responsive to atrial volume. By employing a preload responsive pump, a physiologic morphology pulsatile flow of blood is capable of being delivered into humans through standard size aortic cannulas.

It is to be understood that the form of the invention herewith shown and described is to be taken as a preferred example of the same, and that various changes in the shape, size and arrangement of parts may be resorted to without departing from the spirit of the invention or scope of the subjoined claims.

I claim:

1. In combination, a blood conduit and a pulsatile cardiopulmonary bypass pump, said conduit comprising a tube of biocompatible polymer having a surge chamber portion, a pumping chamber portion and a reservoir portion, a pre-load responsive pulsatile pump having an inlet end, and outlet end and a compression chamber between said inlet and said outlet end, said conduit extending through the compression chamber of said pump, the surge chamber portion of said tube being positioned at the outlet end of said pump and the reservoir portion of said tube being positioned at the inlet end of said pump, an oxygenator, a first tube connected between said oxygenator and said surge chamber portion of said tube, an arterial filter, a second tube connected between said oxygenator and said arterial filter, a third tube connected to the arterial filter and adapted to be connected between said arterial filter and to the aorta of a patient's heart and a forth tube connected to said reservoir portion of said conduit and adapted to be connected to an atrium of a patient's heart said reservoir portion extending.

2. In combination, a blood conduit and a pulsatile cardiopulmonary bypass pump, said conduit comprising a tube of biocompatible polymer having a surge chamber portion, a pumping chamber portion and a reservoir portion, a pre-load responsive pulsatile pump having an inlet end, an outlet end and a compression chamber between the inlet and outlet ends, said conduit extending through the compression chamber of said pump, said pumping chamber portion of the tube being positioned in said compression chamber and having ana extent corresponding to the compression chamber, said surge chamber portion of said tube being at the outlet end of said pump, and the reservoir portion of said tube being positioned at the inlet end of said pump, an arterial filter, a first tube connected between said arterial filter and said surge chamber portion of said tube, a second tube connected to the arterial filter and adapted to be connected to the aorta of a patient's heart, an oxygenator, a third tube connected to said oxygenator and adapted to be connected to the atrium of the patient's heart, and the reservoir portion of said conduit extending outwardly from the inlet end of said pump and being connected to said oxygenator.

* * * * *

UNITED STATES PATENT AND TRADEMARK OFFICE
CERTIFICATE OF CORRECTION

PATENT NO. : 5,300,015

DATED : April 5, 1994

INVENTOR(S) : Thomas M. Runge

It is certified that error appears in the above-identified patent and that said Letters Patent is hereby corrected as shown below:

Column 1, line 41, "©" should read --®--.

Column 4, line 7, after "extending" --outwardly from the inlet end of said pump-- should be inserted.

Column 4, line 17, "ana" should read --an--.

Signed and Sealed this

Twenty-third Day of August, 1994

*Attest:*

BRUCE LEHMAN

*Attesting Officer*   *Commissioner of Patents and Trademarks*